United States Patent
Nystrom

(10) Patent No.: US 10,322,277 B2
(45) Date of Patent: Jun. 18, 2019

(54) CONTRAST MEDIA INJECTOR SYRINGE INLET VALVE SYSTEM

(75) Inventor: Sidney D. Nystrom, Shoreview, MN (US)

(73) Assignee: ACIST MEDICAL SYSTEMS, INC., Eden Prairie, MN (US)

(*) Notice: Subject to any disclaimer, the term of this patent is extended or adjusted under 35 U.S.C. 154(b) by 1011 days.

(21) Appl. No.: 13/300,955

(22) Filed: Nov. 21, 2011

(65) Prior Publication Data

US 2012/0130236 A1 May 24, 2012

Related U.S. Application Data

(60) Provisional application No. 61/416,993, filed on Nov. 24, 2010.

(51) Int. Cl.
| | |
|---|---|
| *A61M 5/28* | (2006.01) |
| *A61M 5/31* | (2006.01) |
| *F16K 15/02* | (2006.01) |
| *F16K 15/06* | (2006.01) |
| *A61B 6/00* | (2006.01) |
| *A61M 5/00* | (2006.01) |

(Continued)

(52) U.S. Cl.
CPC ........... *A61M 39/24* (2013.01); *A61M 5/007* (2013.01); *A61M 5/14546* (2013.01); *A61M 5/285* (2013.01); *F16K 15/026* (2013.01); *F16K 15/06* (2013.01); *A61B 6/548* (2013.01); *A61M 2005/287* (2013.01); *A61M 2005/3106* (2013.01)

(58) Field of Classification Search
CPC ... A61B 6/548; A61M 39/24; A61M 5/14546; A61M 5/007; A61M 2005/287; E21B 33/13; B65D 51/1644; Y10S 215/902; F16K 15/06; F16K 15/026
USPC ......................................... 604/131, 247, 238
See application file for complete search history.

(56) References Cited

U.S. PATENT DOCUMENTS

| 1,496,126 A | * | 6/1924 | Livingstone .......... A61M 5/204 222/372 |
|---|---|---|---|
| 2,538,662 A | * | 1/1951 | Abbott .......................... 604/247 |

(Continued)

FOREIGN PATENT DOCUMENTS

| CA | 2312632 A1 | 12/2001 |
|---|---|---|
| CN | 2187955 Y | 1/1995 |

(Continued)

OTHER PUBLICATIONS

PCT/US2011/061621, International Search Report and Written Opinion dated May 8, 2012, 11 pages.

(Continued)

*Primary Examiner* — Jennifer Dieterle
*Assistant Examiner* — Helene Bor
(74) *Attorney, Agent, or Firm* — Fredrikson & Byron, P.A.

(57) ABSTRACT

A syringe for injecting contrast injection media into a patient. An inlet valve system associated with the syringe, the inlet valve system operable with a contrast injection media having any viscosity within the range of about 1 cP to about 30 cP. An inlet valve system associated with the syringe, the inlet valve system including a valve member having a density of less than or equal to 1 gram per cubic centimeter. A contrast injector system with such a syringe.

28 Claims, 19 Drawing Sheets

(51) Int. Cl.
*A61M 39/24* (2006.01)
*A61M 5/145* (2006.01)

(56) References Cited

U.S. PATENT DOCUMENTS

| | | | |
|---|---|---|---|
| 2,893,390 A * | 7/1959 | Lockhart | A61M 5/286 |
| | | | 604/238 |
| 2,985,182 A | 5/1961 | Williams | |
| 3,299,904 A | 1/1967 | Burke | |
| 3,359,910 A | 12/1967 | Latham, Jr. | |
| 3,411,534 A | 11/1968 | Rose | |
| 3,802,463 A | 4/1974 | Dabney | |
| 3,813,077 A | 5/1974 | Kolic | |
| 3,861,421 A | 1/1975 | Thompson | |
| 3,918,490 A | 11/1975 | Goda | |
| 3,941,128 A * | 3/1976 | Baldwin | 604/238 |
| 4,061,142 A | 12/1977 | Tuttle | |
| 4,282,902 A | 8/1981 | Haynes | |
| 4,484,599 A | 11/1984 | Hanover et al. | |
| 4,585,442 A | 4/1986 | Mannes | |
| 4,645,489 A | 2/1987 | Krumme et al. | |
| 4,969,486 A | 11/1990 | Puzio | |
| 5,113,906 A | 5/1992 | Hoegner | |
| 5,117,870 A | 6/1992 | Goodale et al. | |
| 5,439,452 A | 8/1995 | McCarty | |
| 5,458,581 A | 10/1995 | Hull | |
| 5,533,708 A | 7/1996 | Atkinson et al. | |
| 5,573,515 A * | 11/1996 | Wilson | A61M 5/14216 |
| | | | 128/DIG. 12 |
| 5,611,458 A | 3/1997 | Ogden et al. | |
| 5,769,385 A | 6/1998 | Burrous et al. | |
| 5,851,201 A | 12/1998 | Ritger et al. | |
| 5,901,745 A | 5/1999 | Buchtel | |
| 6,017,332 A | 1/2000 | Urrutia | |
| 6,221,045 B1 * | 4/2001 | Duchon et al. | 604/151 |
| 6,565,535 B2 * | 5/2003 | Zaias et al. | 604/152 |
| 6,656,157 B1 | 12/2003 | Duchon et al. | |
| 7,617,837 B2 | 11/2009 | Wilson et al. | |
| 8,152,780 B2 | 4/2012 | Evans et al. | |
| 8,851,172 B1 * | 10/2014 | Dudzinski | 166/284 |
| 2005/0255426 A1 | 11/2005 | Mariaulle et al. | |
| 2007/0161970 A1 | 7/2007 | Spohn | |
| 2008/0058720 A1 | 3/2008 | Spohn | |
| 2008/0103446 A1 | 5/2008 | Torrance et al. | |
| 2009/0149743 A1 | 6/2009 | Barron et al. | |
| 2010/0130958 A1 * | 5/2010 | Kang et al. | 604/506 |
| 2010/0280462 A1 | 11/2010 | Kommireddy et al. | |
| 2012/0065502 A1 | 3/2012 | Levy et al. | |
| 2013/0053692 A1 | 2/2013 | Barron et al. | |
| 2013/0066202 A1 | 3/2013 | Barron et al. | |
| 2013/0067416 A1 | 3/2013 | Barron et al. | |
| 2014/0107480 A1 | 4/2014 | Spohn et al. | |

FOREIGN PATENT DOCUMENTS

| | | |
|---|---|---|
| CN | 2244409 Y | 1/1997 |
| CN | 101244299 A | 8/2008 |
| CN | 101355975 A | 1/2009 |
| CN | 101461972 A | 6/2009 |
| EP | 1055432 | 11/2000 |
| GB | 2274326 A | 7/1994 |
| JP | S60-02369 A | 1/1985 |
| JP | H07-96033 A | 4/1995 |
| WO | 0024313 A1 | 5/2000 |
| WO | 0155626 A1 | 8/2001 |
| WO | 2005110007 A2 | 11/2005 |
| WO | 2007062315 A2 | 5/2007 |
| WO | 2011002744 A1 | 1/2011 |
| WO | 2011073969 A1 | 6/2011 |

OTHER PUBLICATIONS

"Surface Roughness," chart of amplitude parameters, Retrieved from the Internet <URL:https://en.wikipedia.org/wiki/Surface_roughness> on Sep. 18, 2017, 8 pages.

* cited by examiner

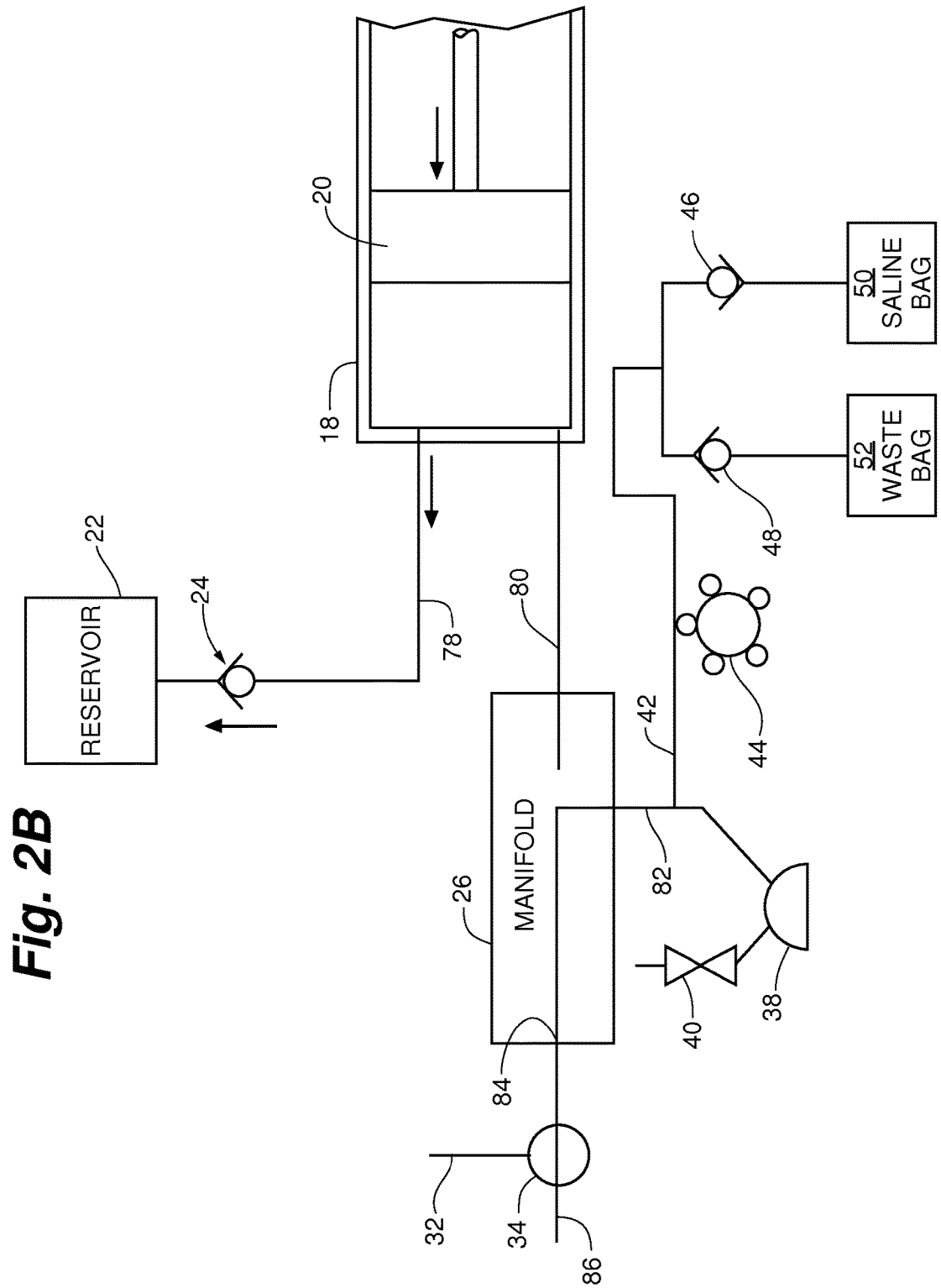

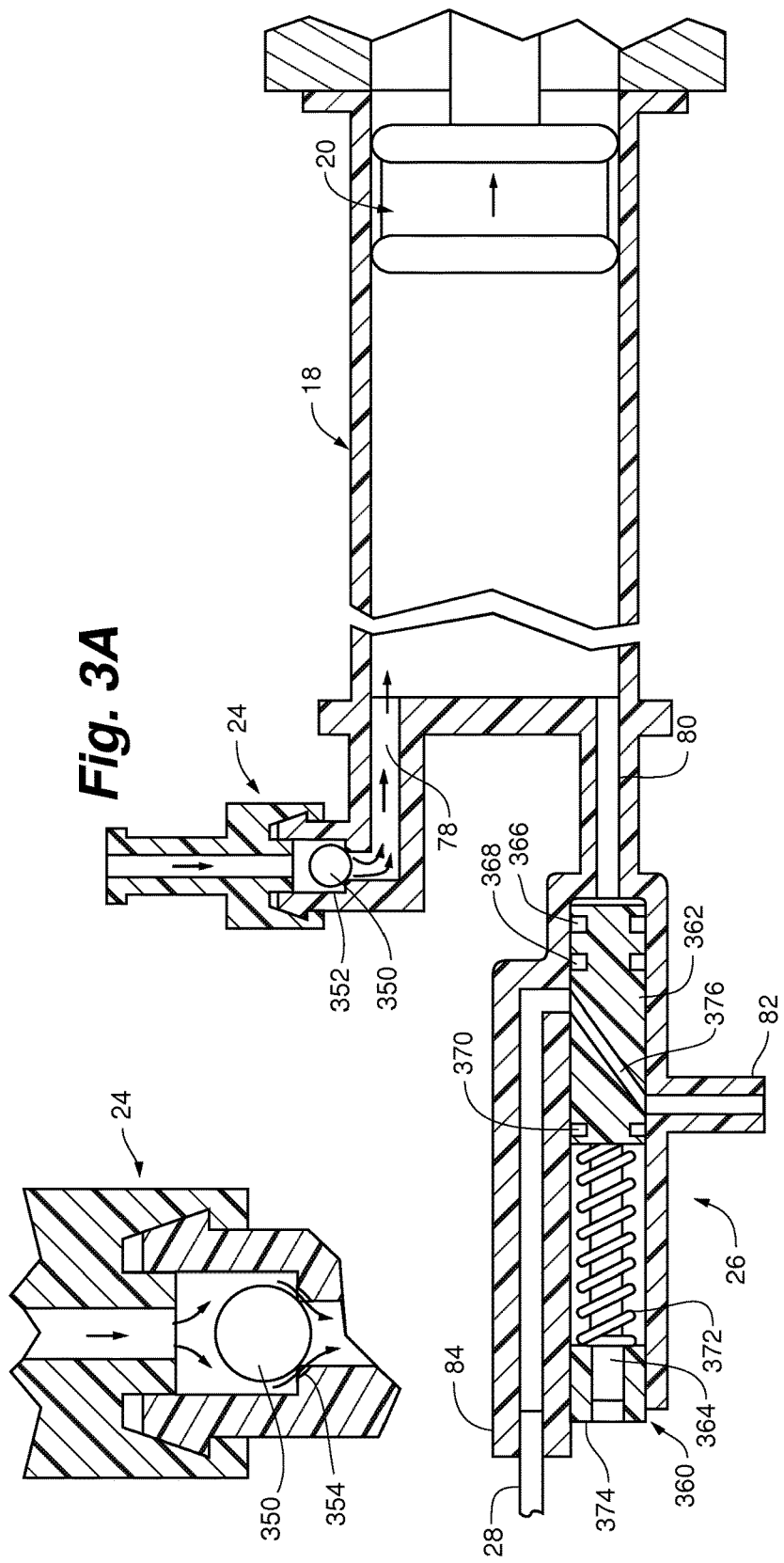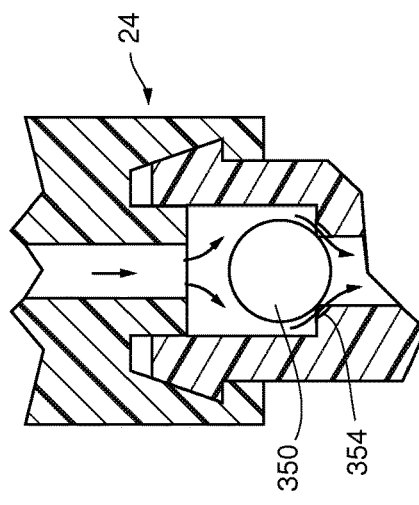

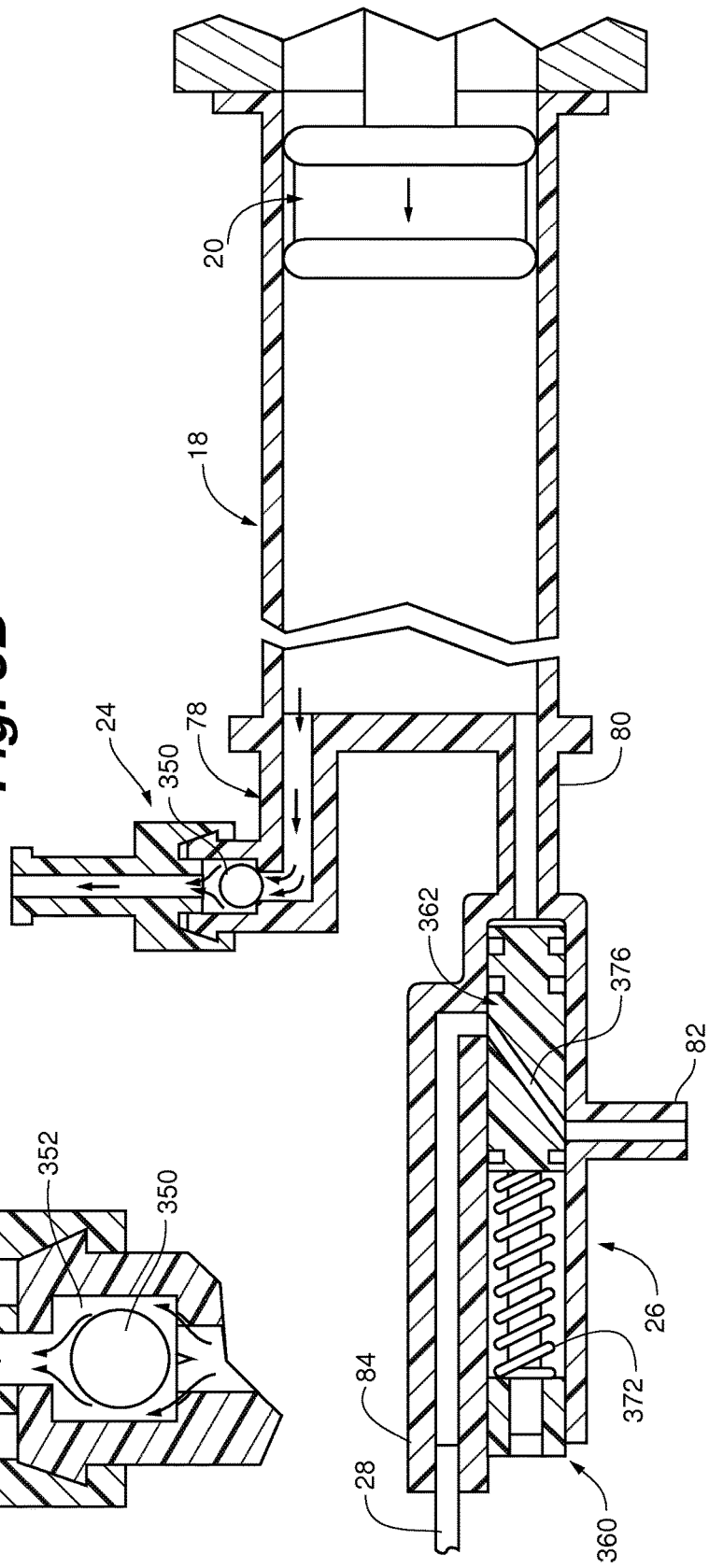

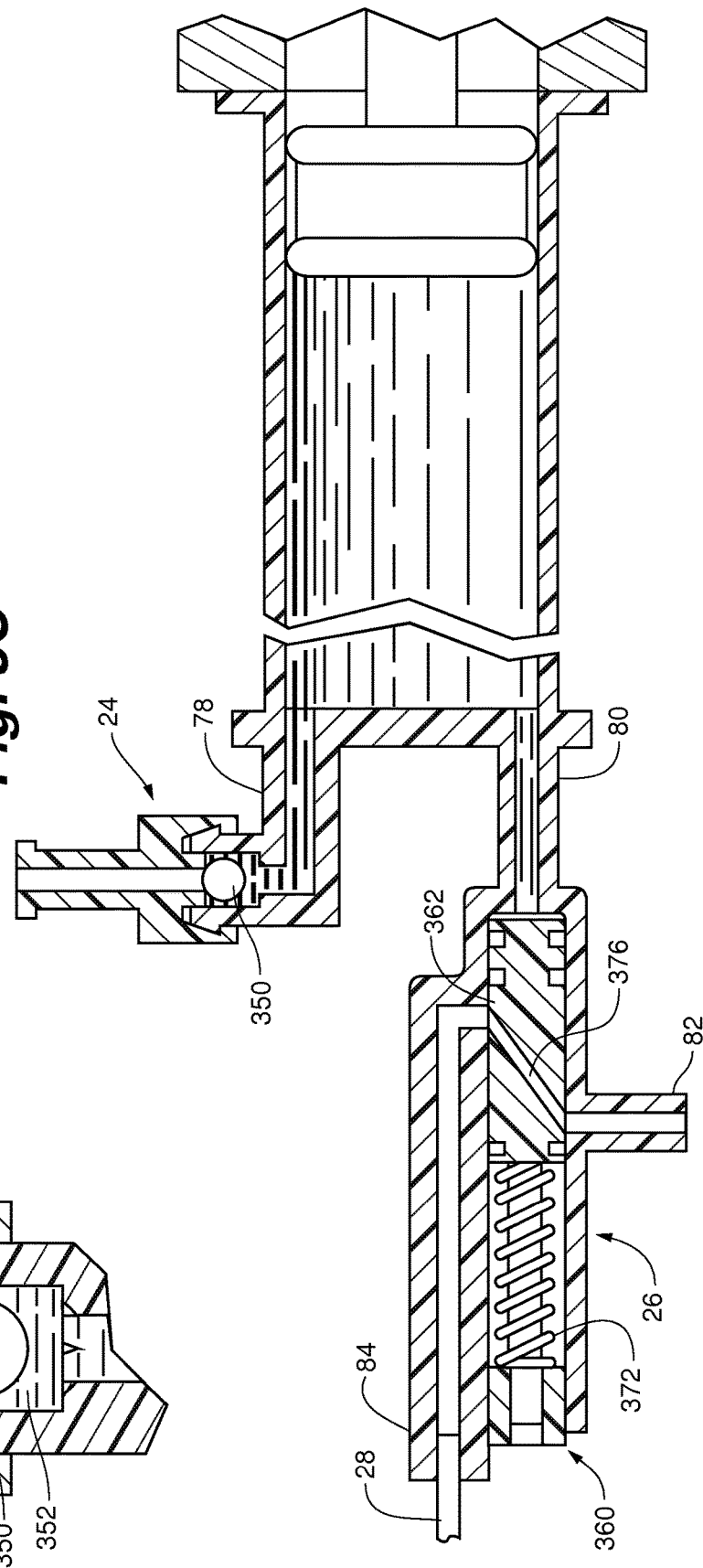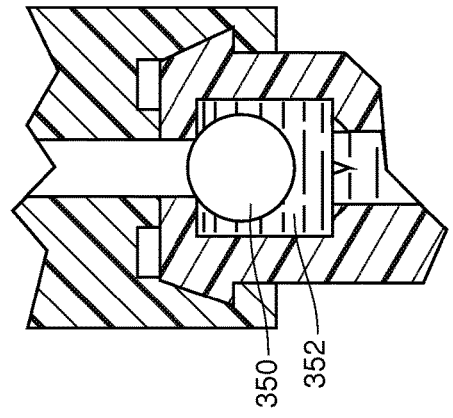

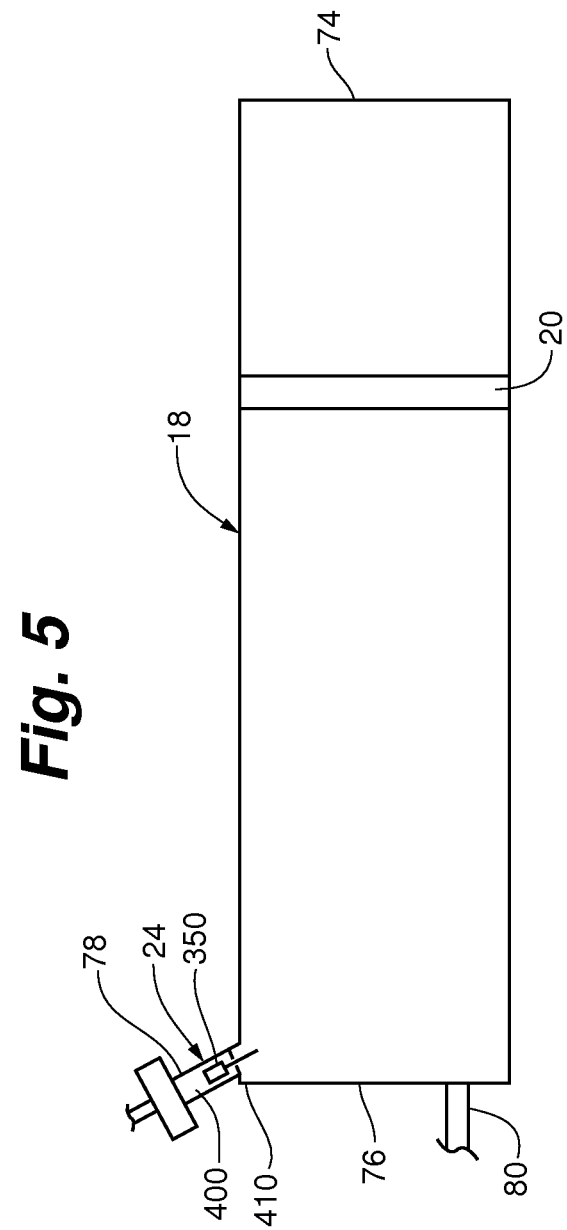

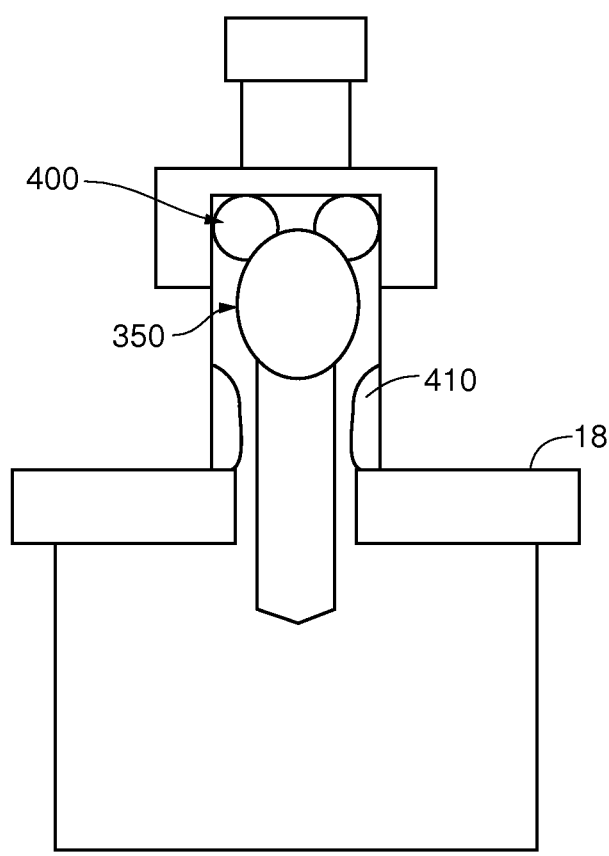

CONTRAST MEDIA INJECTOR SYRINGE INLET VALVE SYSTEM

RELATED APPLICATIONS

The present application claims the benefit of U.S. Provisional Patent Application Ser. No. 61/416,993, titled Contrast Media Injector Syringe Inlet Valve System, and filed Nov. 24, 2010, the contents of which are hereby incorporated by reference.

TECHNICAL FIELD

The present application relates generally to an injector system used to inject a medical fluid such as contrast media into living organisms.

BACKGROUND

Many medical procedures, such as angiographies, involve injecting a contrast media directly into a patient. Angiography is a procedure used in the diagnosis and treatment of cardiovascular conditions including abnormalities or restrictions in blood vessels. During angiography, a radiographic image of the heart or a vascular structure is obtained by injecting contrast media through a catheter into a vein or artery of the patient. The injected contrast media can pass to vascular structures in fluid communication with the vein or artery in which the injection is made. X-rays are passed through the region of the body in which the contrast media was injected. The X-rays are absorbed by the contrast media, causing a radiographic outline or image of the blood vessel containing the contrast media. The contrast media itself is often a viscous fluid with a density greater than water. It is desirable to not inject more contrast media into the patient than is required to successfully perform the imaging procedure. Accordingly, some formulations of contrast media contain a reduced amount of imaging material in a given volume of fluid, thereby making it less viscous and less dense. With these formulations of contrast media, the physician has more options and control to reduce the amount of imaging material injected into a patient.

BRIEF SUMMARY

Various embodiments of the invention are described and shown herein. In one embodiment, the invention includes a contrast media injector system that is adapted to inject contrast media having any viscosity within a wide range of viscosities, and any density within a wide range of densities into a patient. Such an injector system allows a physician to use either high viscosity, high density contrast media, or low viscosity, low density contrast media, depending on patient needs, with a single contrast injector system. In some embodiments, the injector system includes a syringe for delivering the contrast media to the patient. Embodiments of the invention also include a syringe with an inlet valve system that accommodates contrast injection media having any viscosity within a wide range of viscosities and any specific gravity within a wide range of specific gravities. Embodiments of the invention also include replacement syringes with such an inlet valve system for existing contrast injector systems, and methods of injecting a contrast media into a patient.

The details of one or more embodiments of the invention are set forth in the accompanying drawing figures and the description below. Other features, objects, and advantages will be apparent from the description and attachments. The embodiments shown and described are provided for the purposes of illustration, not limitation.

BRIEF DESCRIPTION OF THE FIGURES

FIG. 2B is a diagram illustrating a second operation of a contrast injector system.

FIG. 3A is a side sectional view illustrating the operation of an inlet valve system and manifold during a first operation.

FIG. 3B is a side sectional view illustrating the operation of an inlet valve system and manifold during a second operation.

FIG. 3C is a side sectional view illustrating the operation of an inlet valve system and manifold during a third operation.

FIG. 4A is a side section view illustrating the operation of an inlet valve system during a first operation of a contrast injector system.

FIG. 4B is a side section view illustrating the operation of an inlet valve system during a second operation of a contrast injector system.

FIG. 4C is a side section view illustrating the operation of an inlet valve system during a third operation of a contrast injector system.

FIG. 5 is a side plan view of a syringe with an inlet valve system in accordance with an embodiment of the invention.

FIG. 11 is a side section view of an inlet port with an inlet valve system in accordance with an embodiment of the invention.

DESCRIPTION

Various exemplary embodiments are described herein with reference to the accompanying drawing figures in which like numbers describe like elements. References to above, below, horizontal, vertical, front, back, left, right and the like shall refer to the orientation of the syringe when it is properly positioned in a contrast media injector system.

Embodiments of the invention include a syringe having an inlet valve system able to accommodate a wide variety of contrast media having any viscosity within a wide range of viscosities and/or any density within a wide range of densities, as well as injector systems having such an inlet valve system, as described further below. Such a syringe and inlet valve system can be used with any contrast injector system, including the CVi contrast injector system offered by ACIST Medical Systems, Inc., of Eden Prairie, Minn. Embodiments of a contrast injector system and the general operation of an inlet valve system will be described, followed by a description of an inlet valve system adapted to accommodate a wide variety of contrast media. The pertinent parts of U.S. Pat. No. 6,656,157, titled Infinitely Refillable Syringe, which describes contrast injector systems, are hereby incorporated by reference.

Figure 1:
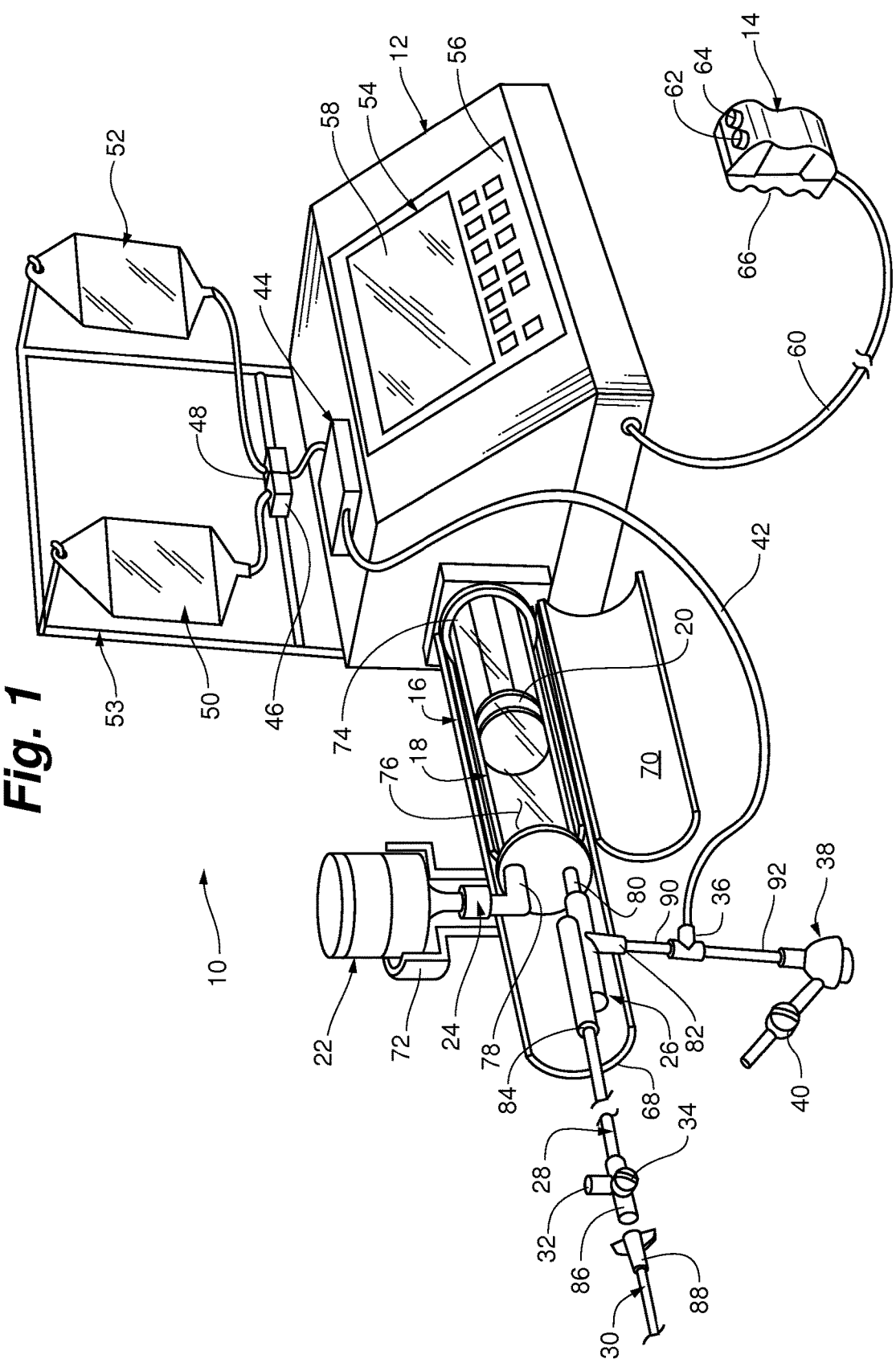
FIG. 1 is a perspective view illustrating a contrast injector system having an inlet valve system in accordance with an embodiment of the invention.

FIG. 1 shows a contrast media injector system 10 for injecting contrast media into a blood vessel under interactive physician control during a medical procedure, such as an angiogram. As shown, system 10 includes main console 12, hand held remote control 14, syringe holder 16, syringe main body 18, syringe plunger/piston 20, radiographic material reservoir (bottle) 22, inlet valve system 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, waste check valve 48, saline bag 50, waste bag 52, and bag support rack 53. It should be noted that system 10 is just one embodiment of contrast media injector system in accordance with the invention. Other embodiments may include a second syringe holder, syringe main body, and syringe plunger in communication with a saline bag instead of the peristaltic pump shown in FIG. 1.

In the embodiments shown, console 12 houses the electrical controls for system 10, together with the motors which drive piston/plunger 20 and peristaltic pump 44. On the front surface of console 12, user interface 54 provides control switches 56 and display 58 through which the user may enter control settings and monitor the operational state of system 10.

Remote control 14 can be connected to console 12 by cable 60 (although in other embodiments remote control 14 may be connected by a wireless connection such as an RF, infrared optic, or ultrasonic link). Remote control 14 is, in the embodiment shown in FIG. 1, a hand-held control which includes reset and saline push button switches 62 and 64, respectively, and flow rate control lever or trigger 66. By squeezing trigger 66, the user can provide a command signal to console 12 to provide a continuously variable injection rate.

As shown in FIG. 1, syringe holder 16 projects from the left hand side of console 12. Syringe holder 16 is preferably a clear material, and includes a half cylindrical back shell 68, a half cylindrical front door 70 (which is shown in open position in FIG. 1), and reservoir holder 72.

The syringe main body 18 generally includes a transparent or translucent plastic cylinder having its open end 74 connected to console 12. A closed end 76 of syringe main body 18 contains two ports: inlet port 78 and outlet port 80. Plunger/piston 20 is movable within syringe main body 18. Plunger/piston 20 is connected to, and driven by a motor located within console 12.

The contrast media reservoir 22 is connected through inlet valve system 24 to inlet port 78. Radiographic contrast material is drawn from reservoir 22 through inlet valve system 24 and inlet port 78 into the pumping chamber defined by syringe main body 18 and plunger/piston 20. Inlet valve system 24 is a one-way valve which permits air to flow from syringe main body 18 back into reservoir 22, but will not permit radiographic contrast material to flow from syringe main body 18 to reservoir 22 when fully closed.

In FIG. 1, the outlet port 80 of syringe main body 18 is connected to manifold 26. Manifold 26 includes a spring biased spool valve which normally connects transducer/saline port 82 and patient port 84. When contrast media is to be injected, the pressure of the contrast media causes the spool valve to change states so that outlet port 80 is connected to patient port 84. Other types of valves that selectively communicate between the contrast media and the saline can be used, including the elastomeric type valves described in Applicant's U.S. Pat. No. 7,617,837.

In the embodiment shown, high pressure tube 28 is a flexible tube which connects patient port 84 to catheter 30. A three-way stop-cock 34 is located at the distal end of tube 28. A rotatable luer lock connector 86 is connected to stop-cock 34 and mates with luer connector 88 at the proximal end of catheter 30. A stopcock 34 either blocks flow between tube 28 and catheter 30, permits flow, or connects medication port 32 to catheter 30 (for use when medication is to be delivered through catheter 30 to the patient).

When catheter 30 is in place in the patient, and an injection of contrast media is not taking place, pressure transducer 38 can monitor the blood pressure through the column of fluid which extends from catheter 30, tube 28, patient port 84, manifold 26, transducer/saline port 82, tubing 90, T-connector 36, and tubing 92. In the embodiment shown, transducer 38 has an associated stop-cock 40 which allows transducer 38 to be exposed to atmospheric pressure during calibration and also allows for removal/expulsion of trapped air so the dome chamber of transducer 38 can be flushed with saline.

Peristaltic pump 44 supplies saline solution from bag 50 through saline check valve 46, tubing 42, T-connector 36 and tubing 90 to saline port 82. When peristaltic pump 44 is operating to supply saline solution, the saline solution is supplied through manifold 26 to patient port 84 and then through tube 28 to catheter 30. Peristaltic pump 44 also operates in an opposite direction to draw fluid from catheter 30 and through tube 28, manifold 26, tubing 90, T-connector 36 and tubing 42 to waste check valve 48 and then into waste collection bag 52. As mentioned above, saline may be alternatively be delivered to the patient with a syringe system instead of a peristaltic pump.

In use, the user (typically a physician) enters into system 10 the safety parameters that will apply to the injection of radiographic contrast material. These safety parameters typically include the maximum amount of radiographic contrast material to be injected during any one injection, the maximum flow rate of the injection, the maximum pressure developed within syringe main body 18, and the maximum rise time or acceleration of the injection. To actuate an injection of contrast material, the user operates remote control 14 by squeezing trigger 66. Within the preset safety parameters, system 10 causes the flow rate of the injection to increase as the force or distance of travel of trigger 66 is increased.

For purposes of illustration, representative operations of system 10 will now be described, including contrast fill, air purge, and patient inject operations. Of course, system 10 can also be configured to perform many other types of operations including, for example, saline flush and patient pressure monitoring operations.

Figure 2A:
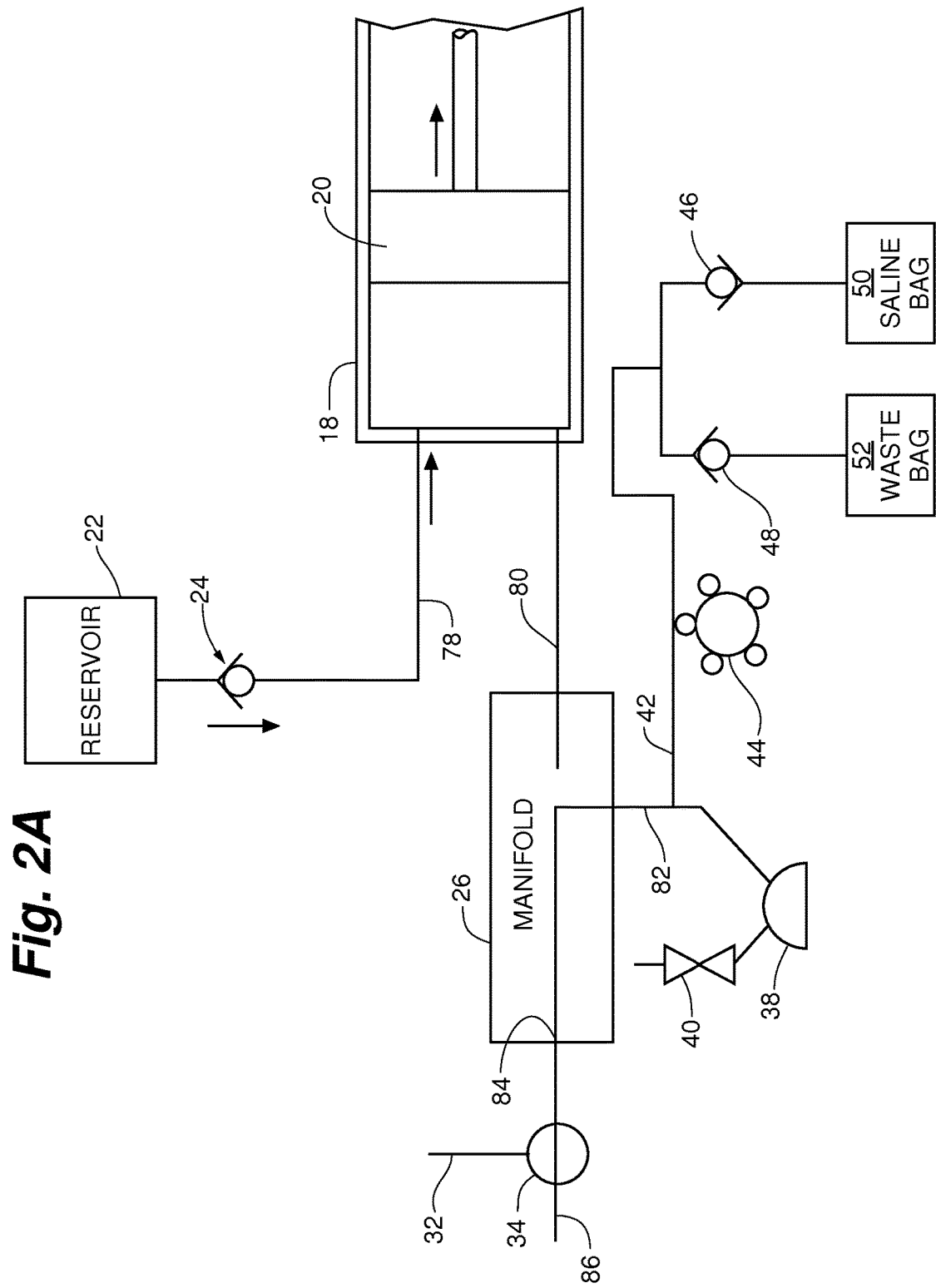
FIG. 2A is a diagram illustrating a first operation of a contrast injector system.

The contrast fill operation illustrated in FIG. 2A involves the filling of syringe main body 18 with contrast media from reservoir (contrast media supply) 22. The contrast fill operation is performed during initial set up of system 10, and may be repeated during operation of system 10 whenever syringe main body 18 is running low on radiographic contrast material. During initial set up of system 10, plunger/piston 20 is initially driven to its furthest forward position adjacent closed end 76 of syringe main body 18. This will expel to the atmosphere the majority of the air which is located within syringe main body 18. Plunger/piston 20 is then retracted, which creates a vacuum within syringe main body 18 which draws contrast material from reservoir 22 through inlet valve system 24 in syringe main body 18 through inlet port 78.

The contrast fill operation typically will result in some air being drawn into or remaining within syringe main body 18. It is important, of course, to prevent air from being injected into the patient through catheter 30. The location of two ports at different elevations allows for a greater amount of safety in preventing air bubbles in the injection. Further, in some embodiments, the syringe can be placed at an angle relative to horizontal (e.g., about 10 degrees from horizontal), such that its closed end, and inlet port 78, are at a higher elevation than its open end. Such an embodiment facilitates air removal from the syringe through inlet port 78.

During the air purge operation, as illustrated in FIG. 2B, plunger/piston 20 travels forward to expel trapped air within syringe main body 18. The air, being lighter than the contrast media, gathers near the top of syringe main body 18. As plunger/piston 20 moves forward, the air is expelled from syringe main body 18 through inlet port 78 and inlet valve system 24. In the embodiment illustrated in FIG. 2B, inlet valve system 24 allows flow of contrast media from reservoir 22 to inlet port 78, but will not allow contrast media to flow in the opposite direction from inlet port 78 to reservoir 22. Inlet valve system 24 will, however, allow air to flow from port 78 to reservoir 22 until sufficient pressure builds in the syringe to close the inlet valve system.

Figure 2C:
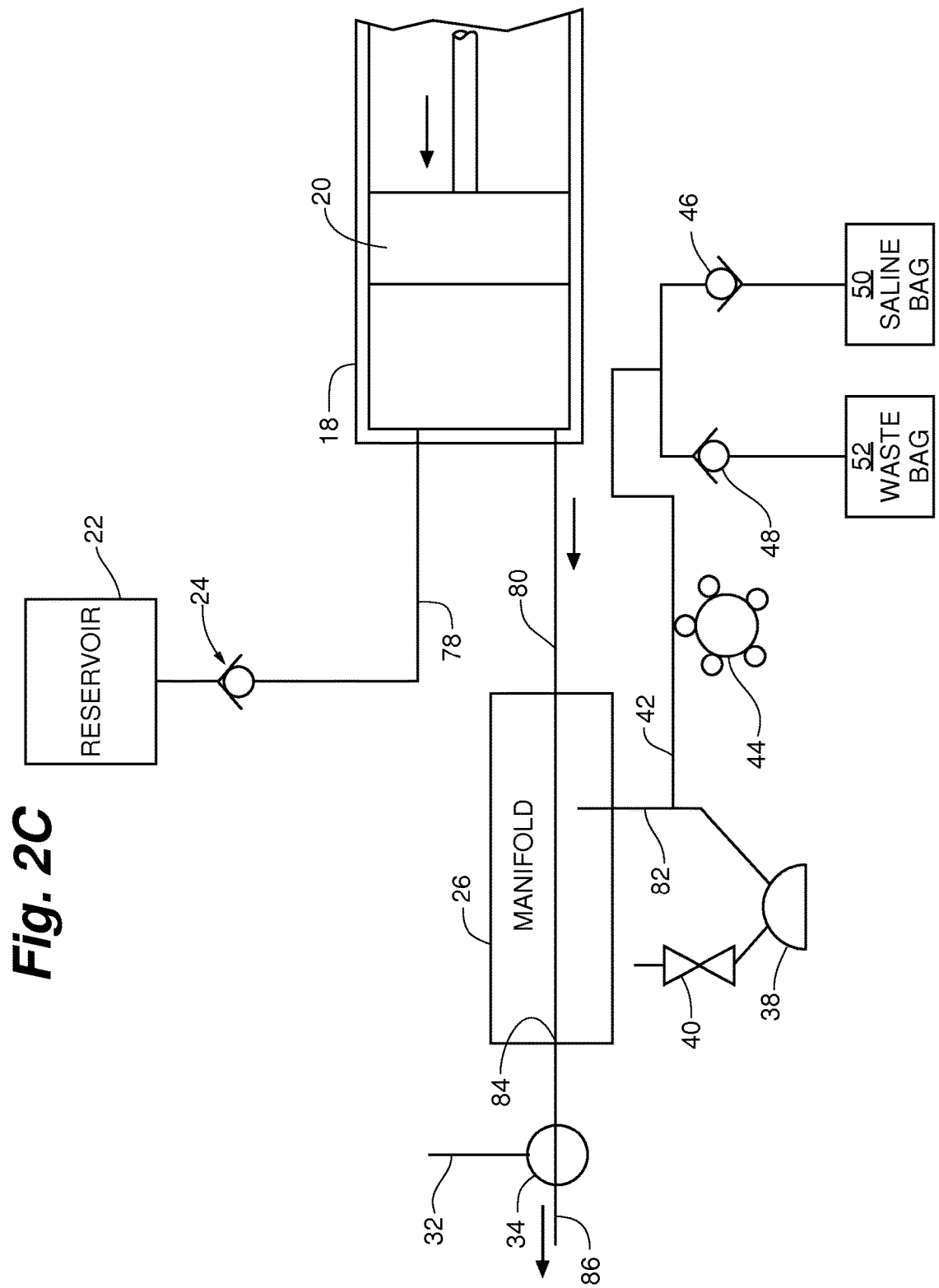
FIG. 2C is a diagram illustrating a third operation of a contrast injector system.

FIG. 2C illustrates a patient inject operation. In this operation, plunger/piston 20 travels forward under the interactive control of the user, who is controlling trigger 66 of remote control 14. The movement of plunger/piston 20 creates hydraulic pressure to force contrast material out of syringe main body 18 through outlet port 80 and through manifold 26 and high pressure tube 28 into catheter 30. As shown in FIG. 2C, syringe outlet port 80 and patient port 84 are connected for fluid flow during the patient inject operation.

In the embodiments shown, manifold 26 contains a valve which controls the routing of fluid connections between patient port 84 and either syringe outlet port 80 or transducer/saline port 82. As shown, manifold 26 can include a spool valve which is spring biased so that patient port 84 is normally connected to transducer/saline port 82 (as illustrated in FIGS. 2A and 2B). When the pressure at syringe outlet port 80 builds with the movement of plunger/piston 20 forward, the bias force against the spool valve is overcome so that syringe outlet port 80 is connected to patient port 84, and transducer/saline port 82 is disconnected the valve within manifold 26 protects pressure transducer 38 from being exposed to the high pressure generated by the patient inject operation. The spool valve opens automatically during the patient inject operation in response to increase pressure exerted on it from the syringe outlet port 80. The spool valve closes and returns to its original position allowing for connection of patient port 84 to transducer 38 when a slight vacuum is applied by retraction of plunger/piston 20 at the end of each patient inject operation. In an alternative embodiment, the valve within manifold 26 is an electromechanical or motor driven valve which is actuated at appropriate times to connect either syringe outlet port 80 or transducer/saline port 82 to patient port 84. In such embodiments, the actuator mechanism can be controlled by console 12. Once again in this alternative embodiment, the valve protects pressure transducer 38 from being exposed to high pressure.

The operation of the contrast injector system can be controlled by any suitable method. In general, the controls will include a digital computer which receives input signals from remote control 14 and front panel controls 56, and provides signals to display 58 to display operation data, alerts, status information and operator prompts, and controls the motion of plunger/piston 20 through a motor drive circuit with a motor.

FIGS. 3A-3D and 4A-4C illustrate the general operation of an embodiment of an inlet valve system 24 and manifold 26 during contrast fill, air purge and patient injection operations.

FIGS. 3A and 4A illustrate an embodiment of an inlet valve system 24, manifold 26, syringe main body 18, and plunger/piston 20 during a contrast fill operation. As shown, inlet valve system 24 includes a valve member 350 which is positioned at a lower seated position within valve chamber 352 in FIGS. 3A and 4B. For purposes of illustration, valve member is represented as a ball in FIGS. 3A-4C. However, as discussed further below, valve member 350 may include a wide variety of shapes and features in accordance with embodiments of the invention. As shown, contrast media is being drawn into syringe main body 18 by the rearward movement of plunger/piston 20. The contrast material flows through passages 354 around valve member 350 and into inlet port 78.

As shown, manifold 26 contains spring loaded spool valve 360, which includes spool body 362, shaft 364, O-rings 366, 368 and 370, bias spring 372, and retainer 374. As shown in FIG. 3A, during the contrast fill operation, bias spring 372 urges spool body 362 to its right-most position toward syringe main body 18. In this position, spool body 362 blocks outlet port 80 of syringe main body 18 while connecting transducer saline port 82 to patient port 84 through diagonal passage 376. O-rings 366 and 368 on the one hand, and O-ring 370 on the other hand, are positioned on the opposite sides of diagonal passage 376 to provide a fluid seal.

FIGS. 3B and 4B illustrate an embodiment of an air purge operation. Syringe main body 18 has been filled with contrast fluid, but also contains trapped air. Plunger/piston 20 is driven forward to force the air out of syringe main body 18 through inlet port 78 and through inlet valve system 24 around the valve member.

During the air purge operation, spool valve 360 is in the same position as in FIG. 3A. Diagonal passage 376 connects transducer saline port 82 with patient port 84. As a result pressure monitoring by pressure transducer 38 can be performed during the air purge (as well as the contrast fill) operation.

FIGS. 3C and 4C illustrate the state of manifold 26 and inlet valve system 24 at the end of the air purge operation and at the beginning of a patient inject operation. In FIG. 3C, all air has been expelled from syringe main body 18. Valve member 350 may float on the radiographic contrast material, so that when all air has been removed and the radiographic contrast material begins to flow out of syringe main body 18 and through inlet port 78 to valve chamber 352, valve member 350 is moved upwards to its upper seated position. Valve member 350 blocks any continued upward flow of contrast media, as is illustrated in FIGS. 3C and 4C.

In the state which is illustrated in FIG. 3C, the pressure within syringe main body 18, and specifically the pressure in outlet port 80 has not yet reached a level at which the bias force of spring 372 has been overcome. As a result, spool body 362 has not yet moved to the left and diagonal passage 376 continues to connect transducer saline port 82 with patient port 84.

Figure 3D:
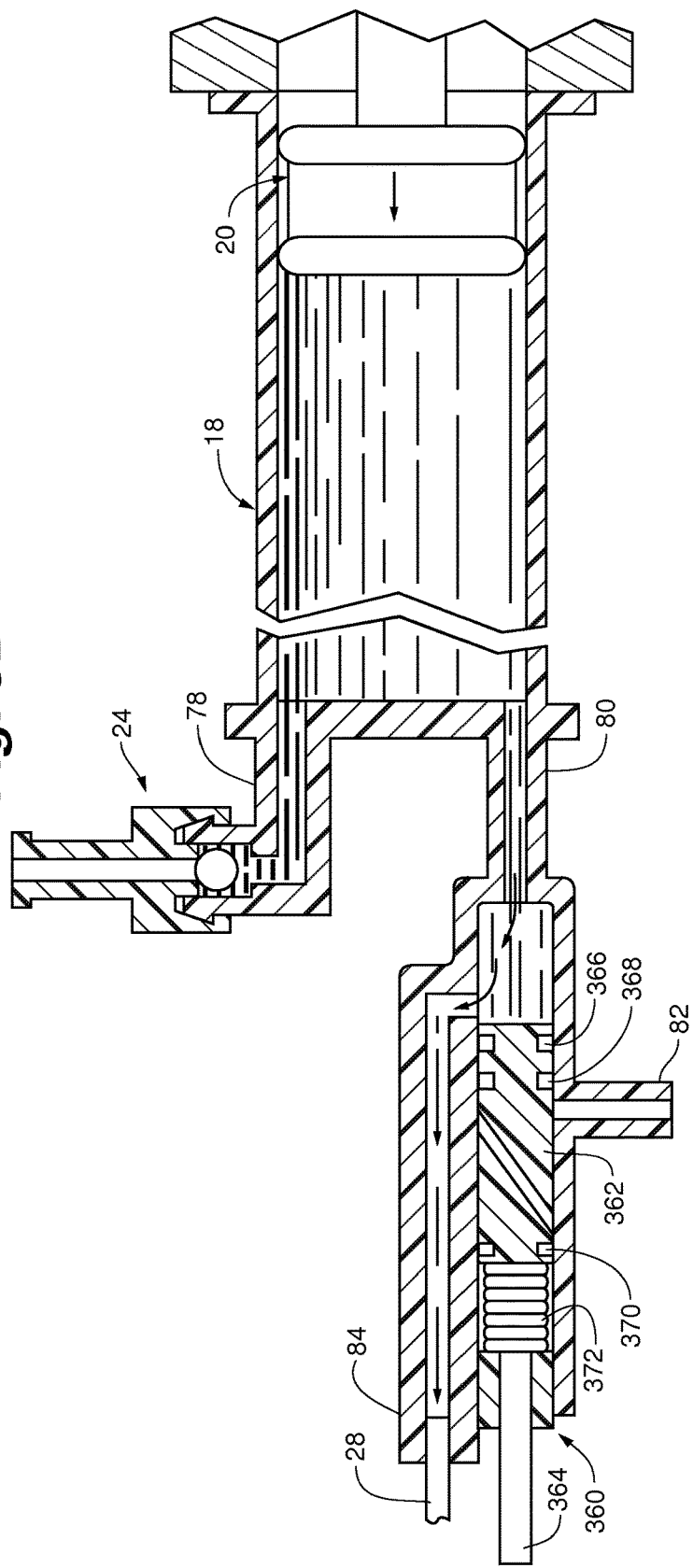
FIG. 3D is a side sectional view illustrating the operation of an inlet valve system and manifold during a fourth operation.

FIG. 3D illustrates an embodiment of a patient inject operation. Plunger/piston 20 is moving forward, and inlet valve system 24 is closed. The pressure at outlet port 80 has become sufficiently high to overcome the bias force of spring 372. Spool body 362 has been driven to the left so that outlet port 80 is connected to patient port 84. At the same time spool body 362 blocks transducer/saline port 82. By virtue of the operation of spool valve 360, the high pressure generated by movement of plunger/piston 20 and syringe main body 18 is directly connected to patient port 84, while saline port 82 and pressure transducer 38 are protected from the high pressure. The pressure to actuate may be variable and determined after manufacture by increasing or decreasing the syringe preload.

Embodiments of the inlet valve system in accordance with the invention will now be further described. FIG. 5 shows a side plan view of a syringe main body 18 having an inlet valve system 24 disposed in an inlet port 78 proximate its closed end 76 and opposite its open end 74. In certain embodiments, the inlet valve system 24 includes a valve member 350, a valve seat 400, and a valve member retaining device 410. The valve member 350 can be selectively positionable against the valve seat 400 to selectively allow contrast media into the syringe main body 18 through the inlet port 78.

As shown in FIG. 5, in some embodiments both the valve member 350 and the valve seat 400 are disposed in the fluid inlet port 78, and the fluid inlet port 78 also serves as a housing for the inlet valve system. The valve member 350 is selectively positionable between the valve seat and the valve retaining device in response to movement of a piston/plunger 20 engaged with the syringe main body 18. When the valve member 350 is fully engaged with the valve seat 400, the inlet valve system is closed. The valve member retaining device 410 is useful for retaining the valve member 350 such that it does not fully enter the syringe main body 18, while also allowing for contrast media and air to flow past it in either direction both when the valve member 350 is in contact with the retaining device 410 and when the valve member 350 is not in contact with the retaining device 410.

Figure 6A:
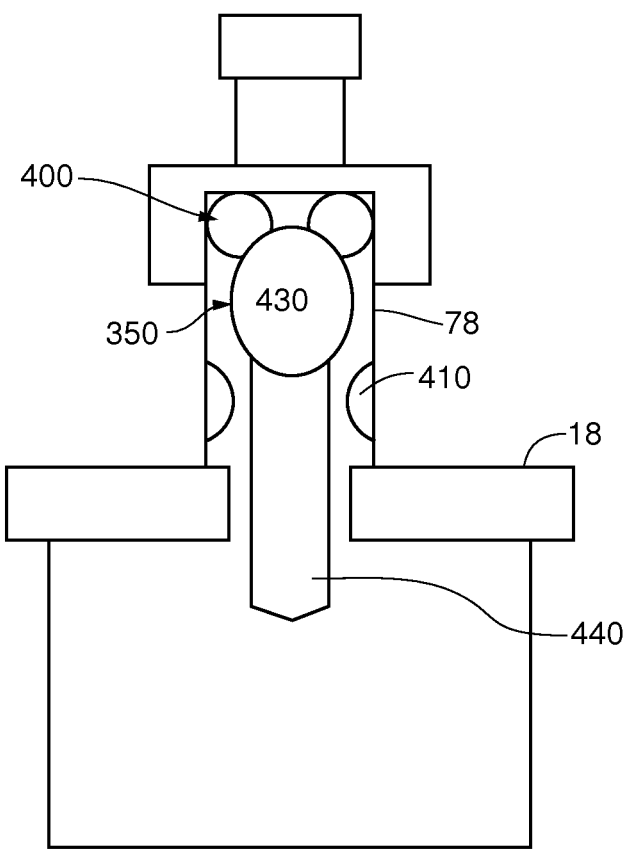
FIG. 6A is a side section view of an inlet port with an inlet valve system in accordance with an embodiment of the invention.
Figure 6B:
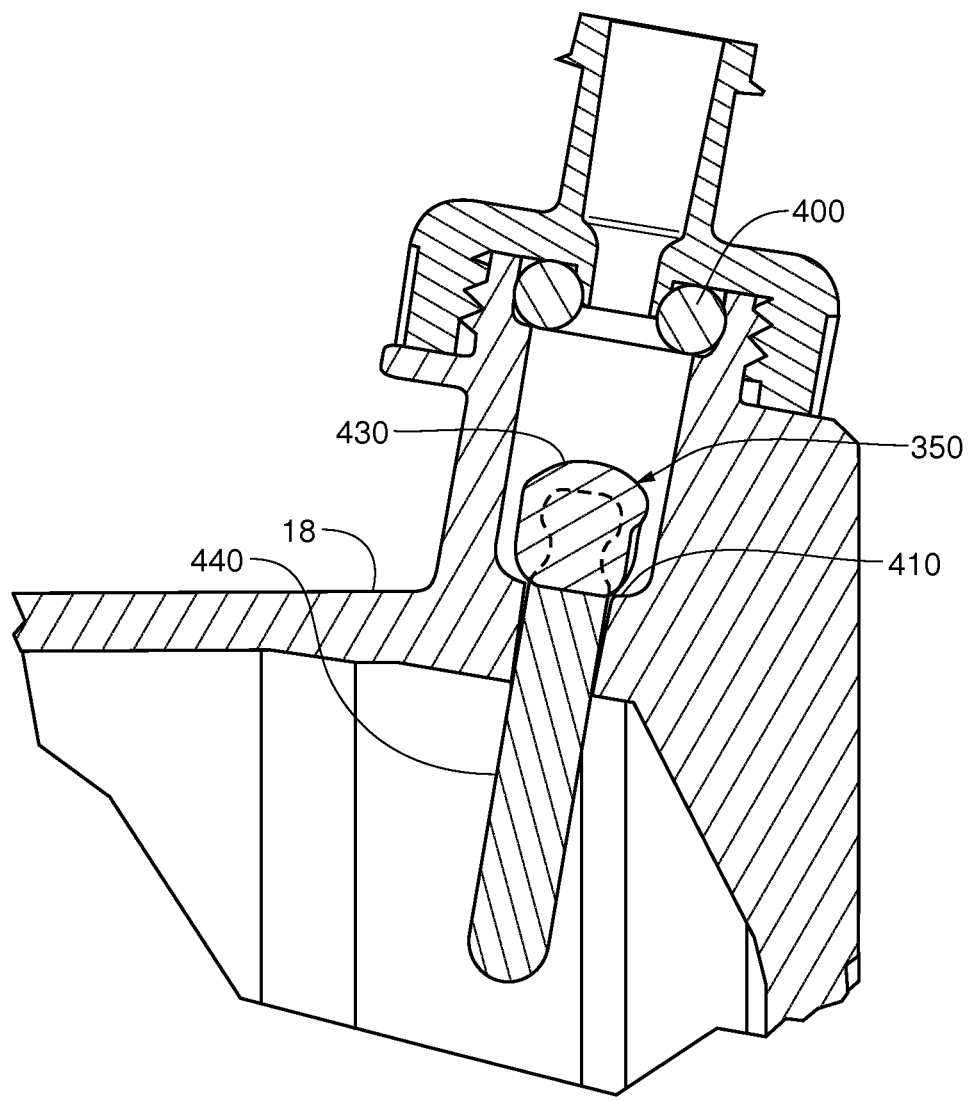
FIG. 6B is a side section view of an inlet port with an inlet valve system during a fluid fill operation in accordance with another embodiment of the invention.
Figure 6C:
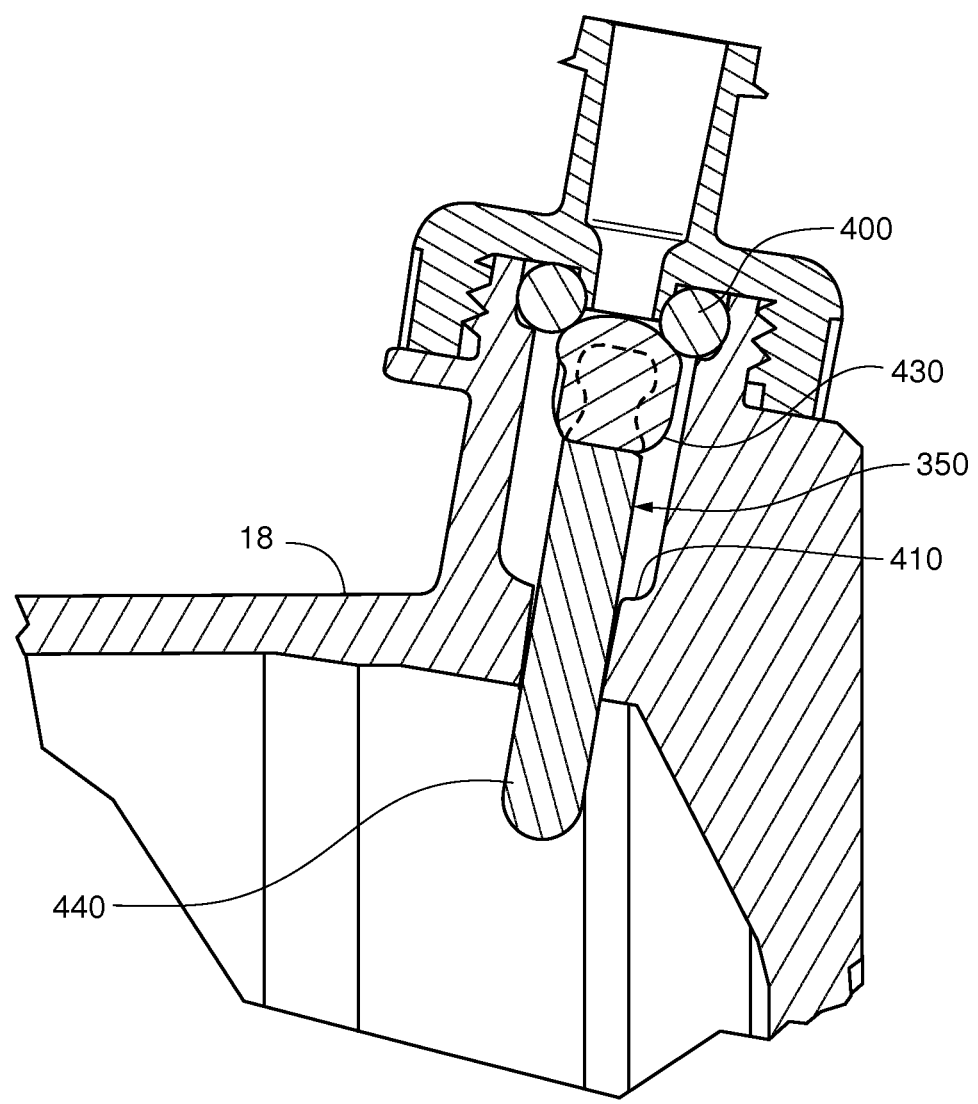
FIG. 6C is a side section view of the inlet port with an inlet valve system during a patient inject operation in accordance with the embodiment of the invention shown in FIG. 6B.

As shown in FIG. 6A, in some embodiments the valve seat 400 is located above the valve member 350 in the fluid inlet port 78, and the valve member retaining device 410 is located below the valve member 350 in the fluid inlet port 78. In such embodiments, when the plunger/piston 20 is drawn back to pull a vacuum the valve member 350 will contact the valve member retention device 410 and contrast media will flow from the contrast media reservoir past the valve member 350 and through the valve member retention device 410 and into the syringe main body 18. Referring back to FIG. 5, as the plunger/piston 20 advances forward toward the closed end 76 of the syringe main body 18 to pressurize the contrast media within the syringe main body 18, the valve member 350 will lift from the valve member retaining device 410 and ultimately seat in the valve seat 400 above the valve member 350. At some pressure, no contrast media can flow past the valve member 350 back into the reservoir. In such a manner, the inlet valve system 24 is automatically open as contrast injection media is delivered into the syringe main body 18 and automatically closed when the contrast injection media is delivered to a patient. FIG. 6B is a side section view of an inlet port with an inlet valve system during a fluid fill operation in accordance with an embodiment of the invention, while FIG. 6C is a view of the inlet port with an inlet valve system during a patient inject operation.

In some embodiments, the inlet valve system 24 is adapted to accommodate a wide variety of contrast media viscosities and specific gravities. Such embodiments are useful for providing physicians with maximum flexibility with contrast media while using a single contrast injector system. In turn, the flexibility can result in less contrast media material having to be used for some patients.

In general, using a steel ball (which generally has a density of between about 7 grams per cubic centimeter and about 8 grams per cubic centimeter) in an inlet valve allows a contrast injector system to accommodate contrast media having a viscosity of between about 4.5 centipoise (cP) and 27.5 cP. The relatively viscous contrast media enables lifting the ball and seating it in a valve seat because the steel ball is denser than the contrast media. However, in some procedures for some patients, it may be desirable to use a contrast media having a viscosity below 4.5 cP. Surprisingly, Applicant has found by using a valve member 350 with a specific gravity less then water (i.e., having a specific gravity of less than one (an average density of less than one gram per cubic centimeter)), the range of viscosities and densities of the contrast media that the contrast injector system is able to accommodate is greatly expanded to include contrast media with a viscosity equivalent to that of water, without sacrificing the ability to accommodate even highly viscous contrast media. In direct contrast to systems with a sinking ball, such embodiments float the valve member in the contrast media rather than relying on the viscosity of the contrast media to push the valve member into a valve seat. The buoyancy force provided by low density valve members in accordance with embodiments of the invention allows for very low viscosity contrast media to be used in the contrast injector system. Accordingly, embodiments of the inlet valve system 24 with such a valve member 350 expands the total range of contrast injection media viscosities operable with the injector system, rather than merely shifting the existing range lower.

In some embodiments, the valve member 350 has a density of less than or equal to 1 gram per cubic centimeter. In other embodiments, the valve member 350 has a density of less than 0.98 grams per cubic centimeter. In yet other embodiments, the valve member 350 has a density of less than 0.96 grams per cubic centimeter. Some embodiments of the invention include an inlet valve system 24 with a valve member 350 comprising, consisting, or consisting essentially of a polymer. In certain embodiments, the invention includes an inlet valve system 24 with a valve member 350 comprising, consisting, or consisting essentially of polypropylene (having a density of about 0.90 grams per cubic centimeter to about 0.99 grams per cubic centimeter), polyethylene (having a density of about 0.90 grams per cubic centimeter to about 0.99 grams per cubic centimeter), or a copolymer thereof. These exemplary materials are also moldable into desired shapes and robust enough to withstand the high pressures achieved in the syringe main body 18, which can reach 1,200 pounds per square inch, for several injection cycles, without undue deformation.

Accordingly, some embodiments of the inlet valve system 24 include a valve member 350 having a density of less than or equal to 1 gram per cubic centimeter, and a valve seat 400 located above the valve member. In such embodiments, the valve member 350 is selectively movable between an open unseated position as the contrast injection media is delivered into the syringe main body 18 through the fluid inlet port 78 and a closed seated position as the contrast injection media is delivered to the patient through outlet port 80.

In some embodiments, the inlet valve system 24 has a valve member 350 that is operable with a contrast injection media having any viscosity within the range of about 1 cP to about 30 cP. By "operable," it is meant that the valve member 350 will unseat from the valve seat 400 during a syringe main body fill operation to allow contrast media to flow past it and will seat against the valve seat 400 during a patient inject operation to block contrast media from flowing back out of the syringe main body 18 through the inlet port 78. In other embodiments, the inlet valve system 24 has a valve member 350 that is operable with any contrast injection media having any viscosity within the range of about 2 cP to about 28 cP. In yet other embodiments, the inlet valve system 24 has a valve member 350 that one is operable with a contrast injection media having any viscosity within the range of about 4 cP to about 28 cP.

Embodiments of the inlet valve system 24 are also able to accommodate a wide range of contrast injection media specific gravities. In some embodiments, the inlet valve system 24 has a valve member 350 that one is operable with a contrast injection media having any specific gravity within the range of about 1 to about 2. In other embodiments, the inlet valve system 24 has a valve member 350 that is operable with a contrast injection media having any density within the range of about 1.2 to about 1.8. In yet other embodiments, the inlet valve system 24 has a valve member 350 that is operable with a contrast injection media having any density within the range of about 1.3 to about 1.5.

Accordingly, embodiments of the invention can accommodate contrast injection media having a viscosity and density the same as essentially water to a highly viscous and dense contrast media. Specific examples include IOMERON-150 (viscosity of 1.4 cP at 37 degrees Celsius, specific gravity of 1.16), RENO-60 (viscosity of 4.0 cP, specific gravity of 1.32), ISOVUE-370 (viscosity of 20.29 cP, specific gravity of 1.405), and IOMERON-400 (viscosity of 27.5 cP, specific gravity of 1.441).

The valve member 350 may take any suitable shape, depending on the geometries of the inlet valve system 24, the inlet port 78, and the valve seat 400. In some embodiments, the valve member 350 has a substantially spherical shape. In other embodiments, the valve member 350 has a substantially cylindrical shape. Further, the valve member 350 need not be symmetrical about any axis, and may include complex and eccentric shapes.

Figure 7A:
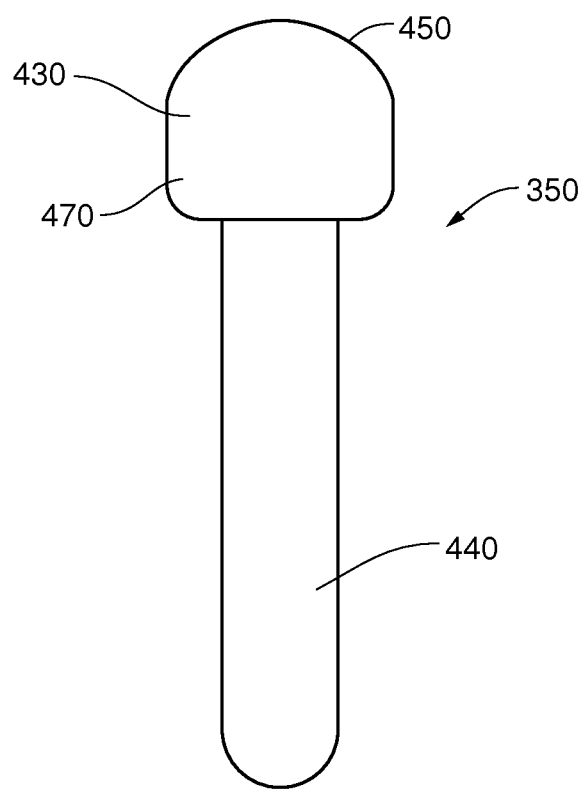
FIG. 7A is a front plan view of a valve member in accordance with an embodiment of the invention.
Figure 7B:
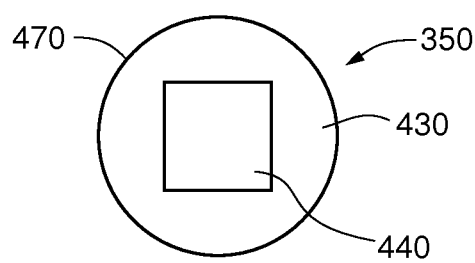
FIG. 7B is a bottom plan view of a valve member in accordance with another embodiment of the invention.

As shown in FIGS. 7A and B, in some embodiments the valve member 350 includes two or more discrete sections, which may be integrally formed or formed separately and joined. In one embodiment, the valve member 350 includes a head section 430 and a tail section 440, which extends in a generally longitudinal direction from the head section. In some embodiments, as shown in FIG. 7A, the head section and the tail section can both include generally cylindrical shapes. In such embodiments, the head section 430 will generally have a larger diameter than the tail section 440. In other embodiments either the head section or the tail section includes a non-cylindrical shape. For example, as shown in FIG. 7B, the head section can include a generally cylindrical shape and the tail section can include a generally square cross-sectional shape. Such a square cross-sectional shape may be advantageous in use with certain air detection systems that include passing an infrared light beam through the inlet valve to detect the presence of air within the valve. Either section may be symmetrical or asymmetrical, and a longitudinal axis of each shape may be aligned or misaligned, or parallel or skewed relative to each other. In some embodiments, the two sections are joined with a radiused surface to promote air movement during an air purge operation. Smooth transitions between the two sections are also useful to reduce the likelihood of small air bubbles clinging to the valve member, which can change its buoyancy properties.

Regardless of the specific shape of either section, embodiments with head and tail sections are useful for providing a valve member 350 with a head section 430 sized to properly seat within the valve seat 400, while changing the center of gravity and/or increasing the mass of the valve member 350 with the tail section 440. Further, in embodiments where the tail section extends downwards towards the syringe main body during use, fluid passing through the inlet valve system will tend to travel along the length of the tail section due to surface tension, which helps to reduce or avoid air bubble formation within the syringe main body during fill operations.

Figure 8:
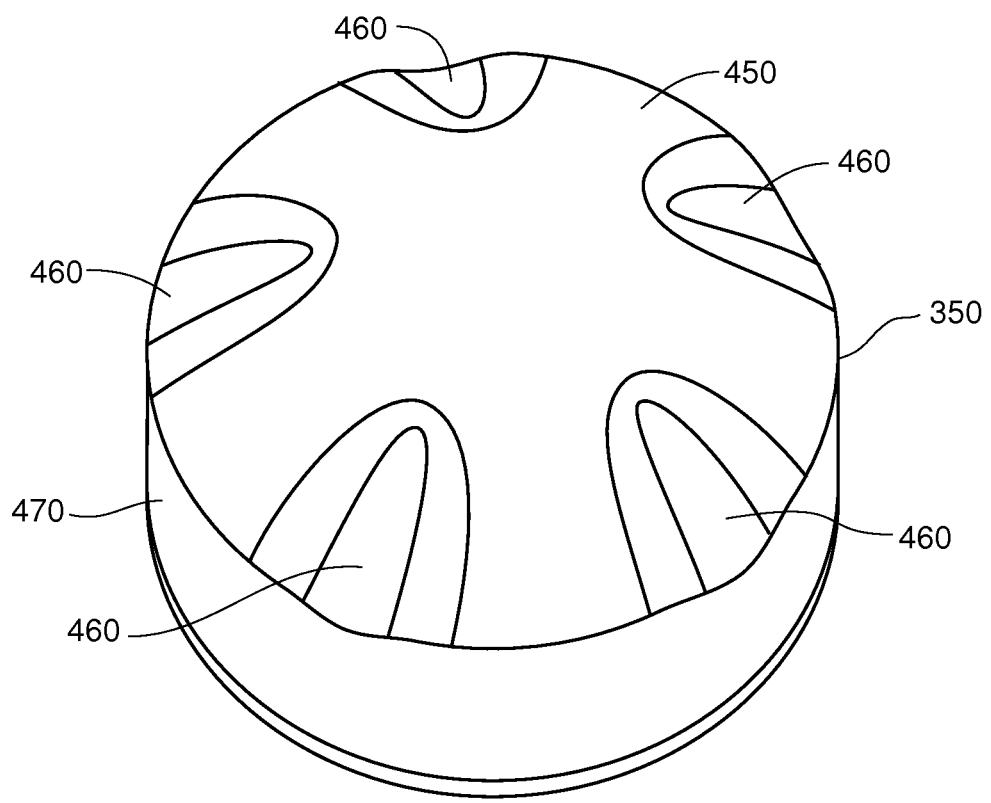
FIG. 8 is a perspective view of a valve member in accordance with an embodiment of the invention.

In some embodiments, the valve member 350 has a seating surface 450 that seats against the valve seat 400. In the embodiment shown in FIG. 7A, the seating surface 450 is the top surface. As shown, the seating surface 450 can include a domed shape. In some embodiments, the seating surface is generally smooth to promote maximum contact between the seating surface and the valve seat 400. However, as shown in FIG. 8, in some embodiments the seating surface is provided with one or more channel(s) 460. Such channel(s) 460 are useful for allowing all of the air and small volumes of contrast injection media (e.g., about 0.1 to about 0.2 milliliters total) to be purged from the inlet port 78 before the valve member 350 is fully seated on the valve seat 400 and no longer allows any fluid communication between the syringe main body side of the inlet port 78 and the reservoir side of the inlet port 78. Allowing a small amount of contrast injection media through the inlet valve system 24 back towards the reservoir may be useful, for example, to reduce false contrast injection media empty reservoir alarms that can be generated if a contrast injection media sensor is placed directly above the seating surface of the valve member 350.

In use, as pressure builds in the syringe main body 18 during an air purge procedure, air will be pushed past the valve member 350 back into the reservoir. During the process the contrast media will eventually contact the valve member 350 and lift it from the valve member retaining device 410 towards the valve seat 400. Eventually the air will be purged and the seating surface 450 of the valve member 350 will contact the valve seat 400. If the seating surface 450 is smooth, no additional contrast injection media will be purged from the system. However, if channel(s) are present, small amounts of contrast media can continue to exit the system through the channel(s) 460. Eventually, the pressure will build in the syringe main body 18 to such an extent that either the valve seat 400 or the seating surface of the valve member 350 will deform such that the fluid pathways through the channel(s) 460 will be closed off and no further fluid can cross the inlet valve system 24.

The channel(s) in the seating surface 450 can include any shape useful for allowing fluid to pass between it and the valve seat 400 at a first contact pressure while allowing inlet valve system 24 to fully close at a second, higher, contact pressure. In the embodiments shown, the channel(s) can include a scallop shape. Further, any number of channel(s) 460 can be provided. In some embodiments, the seating surface 450 has a series of five channels equally spaced about its circumference. In other embodiments, the seating surface can include a truncated icosahedron shape, which resembles a soccer ball with its vertices removed. In such embodiments, space between the facets takes the form of channels that allow fluid to desirably pass between the seating surface and the valve seat as described above.

A valve member with such channel(s) may be provided separately or in combination with the valve member embodiments having a density of 1 gram per cubic centimeter or less described above. Accordingly, in some embodiments, the valve member having a seating surface 450 with channel(s) may include a density of greater than 1 gram per cubic centimeter.

Figure 9:
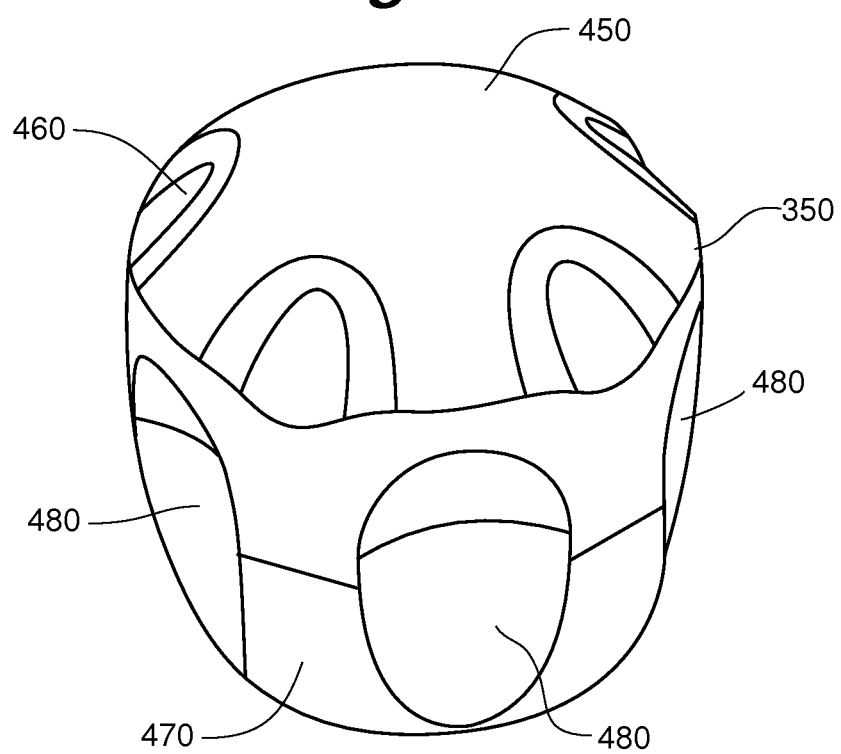
FIG. 9 is a perspective view of a valve member in accordance with an embodiment of the invention.

As show in FIGS. 7A-9, the valve member 350 can also have an outer surface 470, such as a substantially cylindrical outer surface. In some embodiments, this outer surface 470 is smooth. However, as shown in FIGS. 8 and 9, the outer surface 470 can also include one or more grooves 480 to change the center of gravity location and/or decrease the mass of the valve member 350 while retaining a seating surface 450 size suitable for seating against the valve seat 400. The groove(s) 480 in the outer surface 470 can include any shape. In some embodiments, the groove(s) have a flute shape. Any number of groove(s) may be provided. In some embodiments, the outer surface 470 is substantially cylindrical and has a series of five groves equally spaced about its circumference.

Embodiments of the inlet valve system 24 also include a valve member retaining device 410 that restricts the valve member 350 from completely entering the syringe main body 18 when the valve member is not forced against the valve seat (i.e., when the valve system is in the open position). As shown in FIGS. 6A-C, the valve member retaining device 410 can be located below the valve member 350, such that the valve member is movable between a valve seat 400 located above the valve member and the valve member retaining device 410. In some embodiments, the valve member retaining device 410 restricts the valve member 350 from completely entering the main body 18 in the open position, but allows a portion of the valve member to enter the main body 18 in the open position. For example, for embodiments of the valve member having a head section 430 and a tail section 440, the valve member retaining device 410 may be sized to retain the valve member head within the inlet port 78 but allow the tail section 440 (all of the tail section or a portion of the tail section) to pass though it and enter the syringe main body 18. The embodiments of FIGS. 6A-C show the valve member 350 with a portion of a tail section 440 that is within the syringe main body 18 during both a fluid fill operation and a patient inject operation.

The shape and size of the valve member retaining device 410 will ultimately depend on the shape and size of the valve member 350. However, the valve member retaining device should be sized and shaped to allow fluid to pass between it and the valve member regardless of whether or not it is in contact with the valve member. Further, in embodiments having a valve member 350 with a head section 430 and a tail section 440, the valve member retaining device 410 should be shaped to avoid binding the tail section 440. The valve member retaining device 410 can include a symmetrical shape or an asymmetrical shape, and can be complex or eccentric.

Figure 10A:
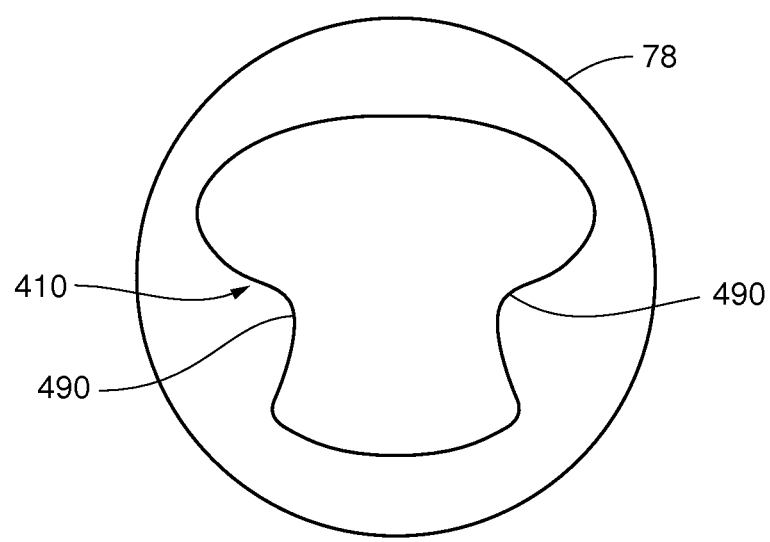
FIG. 10A is a top plan view of a valve member retention device in accordance with an embodiment of the invention.
Figure 10B:
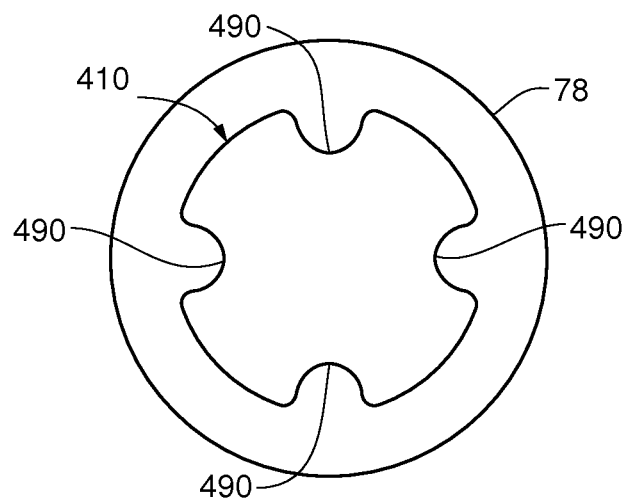
FIG. 10B is a top plan view of a valve member retention device in accordance with another embodiment of the invention.

As shown in FIGS. 10A and B, in some embodiments the valve member retaining device 410 comprises one or more tabs 490 extending into the inlet port 78. These tabs can be located in the inlet port 78 at a position just above the syringe main body 18 and below the valve member and the valve seat 400. Any number of tabs sufficient to retain the valve member can be provided. If the outer surface 470 of the valve member has groove(s) 480 as described above, the number of tabs provided should be different than the number of groove(s) provided to reduce the likelihood that the groove(s) will align with the tabs and allow the valve member to pass through the valve member retention device into the syringe main body 18. An exemplary embodiment is shown in FIG. 10A, which depicts two tabs 490. Such an embodiment may be useful for retaining the valve member 350 with grooves 480 shown in FIG. 9. Further, in embodiments with non-cylindrical tail sections, such tabs may be useful for limiting or preventing rotation of the tail section and, by extension, the valve member. For example, FIG. 10B depicts four tabs 490, which would be useful for limiting or preventing rotation of a tail section with a generally square cross-sectional shape, such as the tail section shown in FIG. 7B. In other embodiments, as shown in FIG. 11, the valve member retaining device 410 includes a funnel shape sized to retain the valve member 350.

The valve seat 400 can include any suitable shape for providing a seat for the valve member 350 and will depend on the shape of the valve member. In some embodiments, the valve seat 400 includes a gasket (e.g., an O-ring comprising a flexible polymer) retained within the inlet port 78, and the seating surface 450 of the valve member seats against the gasket when in the closed position. In other embodiments, when the valve member includes a generally cylindrical shape, the valve seat includes a generally annular flange extending inwardly from the inlet port 78 (and may also optionally include a gasket in apposition to the flange). If the valve member 350 includes a seating surface 450 with at least one channel, the gasket may deform into the channel to seal the channel when the seating surface 450 is pushed into the valve seat by high pressure.

Embodiments of the inlet valve system 24 can also be adapted to facilitate an air detection system provided by a contrast injector system. Some embodiments of contrast injector systems include an air detection system which can include a sensor (such as an ultrasonic or infrared emitter/detector which senses air bubbles) disposed proximate the inlet valve system 24. Such air detection systems are adapted to detect air in the syringe main body 18 and notify the physician of the presence of air and/or disable the injector system. The system may be designed to detect air itself or deduce the presence or absence of air by the position of the valve member 350 relative to the valve seat 400. In some embodiments, the valve member 350 is opaque so that the air detection system can detect its position. In embodiments of a valve member having a head section 430 and a tail section 440, the head section 430 can be opaque and the tail section 440 can be translucent. Such a translucent tail section 440 can be useful for not interfering with other detection systems that may be provided by the contrast injector system.

Embodiments of the invention include syringes having any of the inlet valve system embodiments described herein, as well as contrast injector systems having a syringe with such an inlet valve system. Embodiments of the invention also include a method of injecting contrast injection media into a patient. Such embodiments include one or more of the steps of providing a plunger/piston; providing a syringe engageable with the plunger/piston; providing any of the embodiments of inlet valve systems described herein associated with a fluid inlet port of the syringe; providing a reservoir of contrast injection media; placing the reservoir into communication with the syringe; automatically opening the inlet valve system in response to a rearward movement of the plunger/piston relative to the syringe; automatically actuating the inlet valve system to purge air from the syringe during forward movement of the plunger/piston; and injecting an amount of contrast media into a patient when the inlet valve system is closed. Embodiments of the invention also include method of replacing a syringe on a contrast injector system with a syringe having any of the embodiments of inlet valve systems described herein.

The foregoing description addresses examples encompassing the principles of various embodiments of the present invention. The embodiments may be changed, modified and/or implemented using various types of arrangements. In particular, one or more embodiments may be combined in a single inlet valve system. Those skilled in the art will readily recognize various modifications and changes that may be made to these embodiments of the invention without strictly following the exemplary embodiments and applications illustrated and described herein, and without departing from the scope of the invention. Accordingly, it is not intended that the invention be limited, except as by the appended claims.

What is claimed is:

1. A syringe for injecting contrast injection media into a patient, comprising:
   a main body configured to receive a plunger;
   a fluid outlet port in fluid communication with the main body to deliver the contrast injection media to a patient;
   a fluid inlet port in fluid communication with the main body to deliver the contrast injection media into the main body; and
   an inlet valve system associated with the fluid inlet port, the inlet valve system being open as contrast injection media is delivered into the main body and closed when the contrast injection media is delivered to a patient, the inlet valve system including a valve member with a head section and a tail section extending longitudinally from a first end of the head section, a valve seat located above the valve member and a valve member retaining device located between the head section of the valve member and the main body, the head section on a second end opposite the first end having a seating surface that seats against the valve seat to close the inlet valve system when the contrast injection media is delivered to the patient, the tail section of the valve member extending within the valve member retaining device toward the main body, the valve member selectively movable in response to pressure in the main body between an open unseated position in which the tail section extends into the main body such that the contrast injection media travels along a length of the tail section into the main body and a closed seated position in contact with the valve seat.

2. The syringe of claim 1, wherein the inlet valve system is operable with a contrast injection media having any viscosity within the range of 1 cP to 30 cP.

3. The syringe of claim 1, wherein the inlet valve system is operable with a contrast injection media having any specific gravity within the range of 1 to 2.

4. The syringe of claim 1, wherein the valve member has a density of less than or equal to 1 gram per cubic centimeter, and wherein the inlet valve system is operable with a contrast injection media having any viscosity within the range of 1 cP to 30 cp and any specific gravity within the range of 1 to 2.

5. The syringe of claim 1, wherein the seating surface has at least one channel.

6. The syringe of claim 5, the seating surface having a domed shape.

7. The syringe of claim 5, wherein the channel has a scallop shape.

8. The syringe of claim 1, wherein the valve member has an outer surface, the outer surface having at least one groove.

9. The syringe of claim 1, wherein a portion of the valve member is opaque and a portion of the valve member is translucent.

10. The syringe of claim 1, wherein the inlet valve system is located within the inlet port.

11. The syringe of claim 1, the head section having an outer surface, the outer surface having at least one groove.

12. The syringe of claim 11, wherein the groove has a flute shape.

13. The syringe of claim 1, wherein the valve member retaining device comprises one or more tabs extending into the inlet port.

14. The syringe of claim 1, wherein the valve member retaining device restricts the valve member from completely entering the main body.

15. The syringe of claim 1, wherein the valve seat includes a gasket.

16. The syringe of claim 1, wherein the valve member comprises polyethylene.

17. The syringe of claim 1, wherein the valve member comprises polypropylene.

18. The syringe of claim 1, wherein the tail section of the valve member extends within the valve member retaining device toward the main body when the seating surface seats against the valve seat.

19. A syringe for injecting contrast injection media into a patient, comprising:
   a main body configured to receive a plunger;
   a fluid outlet port in fluid communication with the main body to deliver the contrast injection media to a patient;
   a fluid inlet port in fluid communication with the main body to deliver the contrast injection media into the main body; and
   an inlet valve system associated with the fluid inlet port, the inlet valve system being open as contrast injection media is delivered into the main body and closed when the contrast injection media is delivered to a patient, the inlet valve system including a valve member having a head section and a tail section extending longitudinally from a first end of the head section, a valve seat located above the valve member, and a valve member retaining device located between the head section of the valve member and the main body, the head section on a second end opposite the first end having a seating surface that seats against the valve seat to close the inlet valve system when the contrast injection media is delivered to the patient, the tail section of the valve member extending within the valve member retaining device toward the main body, the valve member selectively movable in response to pressure in the main body between an open unseated position in which the tail section extends into the main body such that the contrast injection media travels along a length of the tail section into the main body and a closed seated position in contact with the valve seat, the inlet valve system operable with contrast injection media having any viscosity within the range of 1 cP to 30 cP.

20. The syringe of claim 19, wherein the inlet valve system is operable with a contrast injection media having a specific gravity within the range of 1 to 2.

21. The syringe of claim 19, wherein the valve member has a density of less than or equal to 1 gram per cubic centimeter.

22. The syringe of claim 19, wherein the seating surface has a domed shape and at least one channel.

23. The syringe of claim 19, wherein the valve member comprises a polymer selected from the group consisting of polypropylene, polyethylene, and a copolymer of polypropylene and polyethylene.

24. The syringe of claim 19, wherein the tail section of the valve member extends within the valve member retaining device toward the main body when the seating surface seats against the valve seat.

25. A contrast media injector system for injecting contrast media into a patient comprising:
a plunger;
a syringe, the syringe having a main body within which the plunger is movable, the syringe having a fluid inlet port;
an inlet valve system associated with the fluid inlet port, the inlet valve system having a valve member with a head section and a tail section extending longitudinally from a first end of the head section, a valve seat positioned above the valve member, and a valve member retaining device located between the head section of the valve member and the main body, the head section on a second end opposite the first end having a seating surface that seats against the valve seat, the tail section of the valve member extending within the valve member retaining device toward the main body, the valve member being automatically actuatable into an open position, in which the tail section extends into the main body such that the contrast injection media travels along a length of the tail section into the main body, as a response to a rearward movement of the plunger relative to the syringe and automatically actuatable to seat the seating surface against the valve seat to close the inlet valve system during a forward movement of the plunger; and
a reservoir of contrast media, the reservoir being positioned relative to the syringe such that the reservoir is in communication with the inlet valve assembly.

26. The contrast injector system of claim 25, wherein the head section has a cylindrical shape and the tail section has a cylindrical shape.

27. The contrast injector system of claim 25, wherein the head section has a cylindrical shape and the tail section has a square cross-sectional shape.

28. The contrast injector system of claim 25, wherein the tail section of the valve member extends within the valve member retaining device toward the main body when the seating surface seats against the valve seat.

* * * * *